(12) United States Patent
Izumi et al.

(10) Patent No.: US 6,248,259 B1
(45) Date of Patent: Jun. 19, 2001

(54) OPTICALLY ACTIVE MONOMER, LIQUID CRYSTAL POLYMER, AND OPTICAL ELEMENT

(75) Inventors: Kyoko Izumi; Shusaku Nakano; Amane Mochizuki, all of Osaka (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 09/402,539

(22) PCT Filed: Apr. 27, 1998

(86) PCT No.: PCT/JP98/01934

§ 371 Date: Oct. 6, 1999

§ 102(e) Date: Oct. 6, 1999

(87) PCT Pub. No.: WO98/49171

PCT Pub. Date: Nov. 5, 1998

(30) Foreign Application Priority Data

Apr. 28, 1997 (JP) .................................................. 9-124899

(51) Int. Cl.[7] .......................... C09K 19/34; C09K 19/52; F21V 9/00
(52) U.S. Cl. ................ 252/299.61; 252/299.01; 252/582
(58) Field of Search .................. 252/299.61, 299.01, 252/582

(56) References Cited

U.S. PATENT DOCUMENTS 5,744,057 * 4/1998 Meyer et al. ............... 252/299.01
5,780,629 * 7/1998 Etzbach et al. ..................... 544/296

FOREIGN PATENT DOCUMENTS

| 9-20781 | 1/1997 | (JP) . |
| 95/16007 | 6/1995 | (WO) . |
| 95/24454 | 9/1995 | (WO) . |
| 97/00600 | 1/1997 | (WO) . |

* cited by examiner

Primary Examiner—C. H. Kelly
(74) Attorney, Agent, or Firm—Sughrue, Mion, Zinn, Macpeak & Seas, PLLC (57) ABSTRACT

To obtain a monomer having a large torsion force, to obtain a liquid crystal polymer which is excellent in a film-forming property, can easily control a helical pitch of a cholesteric phase, can form a grandjean orientation in a good monodomain state by an orientation treatment in a short time such as few minutes, and can stably fix it in a glass state, and to obtain an optical element having a circular dichroism, represented by the following formula (a), comprising a solidified product of the liquid crystal polymer, which is thin and light, is hard to change the oriented state such as pitch, etc., at a practical temperature, and has excellent durability and storage stability.

An optically active monomer represented by

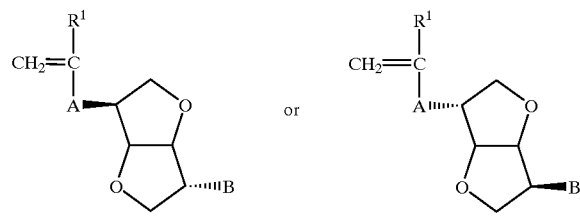

(wherein $R^1$ represents a hydrogen atom or a methyl group, and A and B represent an organic group); a side chain type liquid crystal polymer having a structural unit comprising the optically active monomer; and an optical element showing a circular dichroism having a solidified layer of a grandjean oriented cholesteric liquid crystal phase comprising the liquid crystal polymer.

7 Claims, 7 Drawing Sheets

OPTICALLY ACTIVE MONOMER, LIQUID CRYSTAL POLYMER, AND OPTICAL ELEMENT

TECHNICAL FIELD

The present invention relates to an optically active monomer and a liquid crystal polymer thereof suitable for forming a liquid crystal display, and to an optical element having a circular dichroism using the polymer.

BACKGROUND ART

A polarizing film prepared by adsorbing a dichromatic dye, etc., to a stretched film, such as a stretched polyvinyl alcohol film, etc., cannot be effectively used because at least 50% of an incident light is absorbed, and thus it is difficult to increase a luminance and decrease a consumed electric power of a liquid crystal display device, etc. As a result, an optical element having a circular dichroism has been expected. This is because a helical axis of a liquid crystal molecule causes a vertical grandjean orientation to the optical element, in the natural light striking in parallel to the helical axis (incident angle: 0 degree), about a half of the light of a certain wavelength is reflected as a right (or left) circularly polarized light, residual about a half of the light is transmitted as a left (or right) circularly polarized light, the wavelength λ is determined by the equation λ=n·p (wherein n is a mean refractive index of liquid crystal and p is helical pitch of a cholesteric phase), the right or left reflected circularly polarized light is determined by the helical state of the cholesteric phase and coincides with the circulation direction of the helix, and thus there is a possibility that the reflected light can be utilized in addition to the transmitted light by the separation of the natural light as described above.

Hitherto, as an optical element having a circular dichroism, an optical element formed by enclosing a liquid cholesteric liquid crystal made up of a low molecular weight material between substrates such as glasses in an oriented state and an optical element made up of a liquid crystal polymer showing a cholesteric liquid crystal phase are known as disclosed in Japanese Patent Publication (unexamined) No. 55-21479 and U.S. Pat. No. 5,332,522.

However, in the former low molecular weight material, because substrates are used, the optical element becomes thick and heavy and there is a problem of hindering light-weighting and thinning of the liquid crystal display. Also, there is a problem that the orientation state of the liquid crystal, for example, a pitch thereof is liable to be changed by the change of temperature, etc.

On the other hand, in the case of using the latter liquid crystal polymer, it is difficult to obtain a solid material such as a film of a good oriented state as a low molecular weight material, a long time such as several hours, etc., is required for the orientation treatment, the glass transition temperature thereof is low, or the durability is insufficient, resulting in poor practical use. Thus, in any cases, it is difficult to obtain an optical element having a circular dichroism in a solid state, in particular, the optical element for visible light.

For the purpose of improving the solid state, various attempts of combining monomers, in particular changing monomers having a cholesteric phase-imparting property have been made, but at present the problems of being poor in liquid crystal orienting property and heat resistance have not yet been solved. For example, to obtain a cholesteric type liquid crystal polymer wherein the selected reflected wavelength is in a visible light region, it is necessary that the copolymerization ratio of a monomer having the cholesteric phase-imparting property is at least about 15% by weight, and liquid crystal property and heat resistance of the polymer obtained are greatly decreased.

Accordingly, an object of the present invention is to provide a monomer having a large torsion force defined by $10^4/[\text{selectively reflected wavelength (nm)} \times \text{copolymerization ratio (mol \%)}]$, to provide a liquid crystal polymer using the monomer, which is excellent in a film-forming property, can easily control a helical pitch of a cholesteric phase, can form a grandjean orientation in a good mono-domain state by an orientation treatment of a short time such as few minutes, and can stably fix it in a glass state, and to provide an optical element having a circular dichroism made up of a solidified product of the liquid crystal polymer, which is thin and light, is hard to change the oriented state such as pitch, etc., at a practical temperature, and has excellent durability and storage stability.

DISCLOSURE OF INVENTION

The present invention provides an optically active monomer represented by the following formula (a):

(wherein $R^1$ represents a hydrogen atom or a methyl group, A represents an organic group, and B represents an organic group represented by the formula (2a) mentioned below);
a side chain type liquid crystal monomer having a structure unit comprising the above-descried optically active monomer, which may show a cholesteric liquid crystal phase; and an optical element comprising the liquid crystal polymer, which has a solid layer of grandjean oriented cholesteric liquid crystal phase and shows a circular dichroism.

BEST MODE FOR CARRYING OUT THE INVENTION

The optically active monomer of present invention is represented by the following formula (a):

(wherein $R^1$ represents a hydrogen atom or a methyl group, A represents an organic group, and B represents an organic group represented by the formula (2a) mentioned below).

The particularly preferred optically active monomer from the point of a torsion force is a monomer represented by the following formula (b):

Accordingly, the optically active monomer represented by the formula (b) is the optically active monomer of formula (a) described above, wherein A is represented by the formula (a1): $COO(CH_2)_m R^2 Z$, and B is represented by the following formula (a2):

In the above-described formula (b), m is an integer of 1 to 6; $R^2$ is represented by the following chemical formulae, and Z represents COO— or O—:

Also, Y represents OCO— or O—; $0 \leq n \leq 3$; and $R_3$ represents —$C_d H_{2d+1}$ when n is 0 and represents —$OC_d H_{2d+1}$, —H, —CN, or —Cl when $1 \leq n \leq 3$, wherein d is $1 \leq d \leq 3$.

The particularly preferred optically active monomer is one wherein $R^2$ in the formula (b) is as follows:

and B in the following formula (a) is as follows:

The optically active monomer of the present invention represented by the above-described formula (b), accordingly represented by the formula (a), can be synthesized by an appropriate method. For example, a synthesis example of the monomer represented by the above-described formula (b1) is shown below.

That is, as the reaction formula described below, ethylene chlorohydrin and 4-hydroxybenzoic acid are refluxed under heating in an aqueous alkali solution using potassium iodide as a catalyst to obtain 4-(2-hydroxyethoxy)benzoic acid, the product is then reacted with vinyl (meth)acrylate in THF (tetrahydrofuran) having added thereto lipase PS and a small amount of p-methoxyphenol to form 4-(2-propenoyloxyethoxybenzoic acid) (meth)acrylate, and by esterifying the (meth)acrylate thus obtained in methylene chloride with an isosorbide derivative in the presence of DCC (dicyclohexylcarbodiimide) and DMAP

(dimethylaminopyridine), the desired product of the formula (b1) can be obtained.

(b1)

In addition, the isosorbide derivative added in the final step of the above-described reaction can be obtained by, for example, a method of adding DHP (3,4-dihydro-2H-pyran) to THF having dissolved therein isosorbide and a small amount of p-toluenesulfonic acid (TsOH)•hydrate to protect the hydroxyl group at one side with THP (tetrahydropyranyl), reacting the isosorbide and 4-cyanobenzoic acid in ethyl acetate in the presence of DCC and DMAP, separating the THP-protected ester from a filtrate formed by filtrating off DCC urea from the reaction mixture, and removing the protective group of THP by treating the product with hydrochloric acid, etc. The reaction steps are illustrated below.

Accordingly, other optically active monomers represented by the formula (a) can be synthesized using appropriate raw materials each having a desired introducing group according to the above-described reaction.

The liquid crystal polymer of the present invention is prepared using at least the optically active monomer represented by the formula (a). Therefore, the liquid crystal polymer has the structural unit comprising at least the optically active monomer represented by the formula (a), that is, the monomer unit represented by the following formula (c), and is a side-chain type liquid crystal polymer based on at least such a monomer unit and, in particular, a liquid crystal showing a cholesteric liquid crystal phase.

Formula (c):

(wherein $R^1$, A, and B are according to the case of the formula (a)).

Accordingly, the liquid crystal polymer of the present invention can be obtained as a homopolymer or a copolymer using one or more kinds of the optically active monomers represented by the formula (a); a copolymer using one or more kinds of the optically active monomers represented by the formula (a) together with one or more kinds of other monomer(s) such as monomers forming polymers showing a nematic liquid crystal phase and other kinds of optically active monomers; and a mixed polymer obtained by mixing these polymers as an appropriate combination.

The liquid crystal polymer of the present invention can be preferably used for forming an optical element showing various optical functions, such as a retardation film, a notch filter, a film showing a circular dichroism, etc. In particular, the liquid crystal polymer showing a cholesteric liquid crystal phase can be preferably used for forming an optical element having a circular dichroism by subjecting the liquid crystal polymer to a grandjean orientation.

The liquid crystal polymer which can be preferably used for forming an optical element having a circular dichroism, particularly one having a selective reflection wavelength in a visible light region, is a copolymer of one or more kinds of the optically active monomers represented by the above-described formula (b) and one or more kinds of monomers forming a polymer showing a nematic liquid crystal phase as the constituents, and particularly a copolymer containing 1 to 40% by weight of the optically active monomer unit represented by the formula (b) and 99 to 60% by weight the nematic series monomer.

If the content of the above-described optically active monomer unit in the copolymer is too small, the copolymer formed becomes poor in the property of forming the cholesteric liquid crystal phase, and if the content of the optically active monomer is excessive, the copolymer becomes poor in the liquid crystal property. From such a point, the copolymerization ratio of the optically active monomer unit is preferably 2 to 38% by weight, more preferably 3 to 35% by weight, and particularly preferably 5 to 30% by weight.

Also, a mixture of a polymer using the optically active monomer(s) represented by the above-described formula (b) as the whole monomer component and a polymer using the monomer(s) forming the polymer showing the nematic liquid crystal phase as the whole monomer component can be preferably used as the optical element having a circular dichroism, particularly, one having the selective reflection wavelength in a visible light region. The mixing ratio of both the polymers is according to the case of the above-described copolymer.

There is no particular limitation on the monomer forming the polymer showing the nematic liquid crystal phase described above and an appropriate monomer can be used. However, from the point of the optical characteristics, etc., a monomer represented by following formula (d) can be preferably used as the monomer.

wherein $R^4$ represents a hydrogen atom or a methyl group; e is an integer of 1 to 6; X represents $CO_2$— or OCO—; and p and q are 1 or 2 and satisfy p+q=3.

The monomer represented by the above-described formula (d) can also be synthesized using appropriate raw materials having a desired introduction group according to the case of the formula (a) described above. The molecular weight of the liquid crystal polymer which can be preferably used for the formation of an optical element, particularly an optical element having the liquid crystal polymer as a solidified layer made up of a cholesteric liquid crystal phase, etc., is 2,000 to 100,000, and particularly from 2,500 to 50,000, based on a weight average molecular weight. If the molecular weight is too small, there is a case that the liquid crystal polymer is poor in the film-forming property, and if the molecular weight is excessive, there is a case that the liquid crystal polymer becomes poor in the orientation property, and particularly in the formation of a monodomain via a rubbing orientation film, whereby a uniform orientation state is hard to be formed. For the formation of the optical element, from the points of the durability of the element, the stability or the unchanging property of the orientation characteristics, such as pitch, to the temperature change, etc., at the practical use, the liquid crystal polymer having a glass transition temperature of at least 80° C. can be preferably used.

The preparation of the liquid crystal polymer of a homopolymer-type, a copolymer-type, etc., can be carried out according to an ordinary polymerization system of an acrylic monomer, such as a radical polymerization system, a cation polymerization system, and an anion polymerization system. In addition, in the case of applying a radical polymerization system, various polymerization initiators can be used. Of those, azobisisobutyronitrile, benzoyl peroxide, etc., which have a decomposition temperature not so high and not so low and is decomposed at an intermediate temperature, are preferably used in the point of the stability of the synthesis, etc.

In the liquid crystal polymer of the present invention, the pitch of the cholesteric liquid crystal is changed based on the content of the monomer unit represented by the formula (a) in the copolymer or the polymer mixture thereof. Because the wavelength showing the circular dichroism is determined by the pitch, the wavelength showing the circular dichroism can be controlled by controlling the content of the monomer unit represented by the formula (a), particularly represented by the formula (b).

Also, the wavelength region showing the circular dichroism can be controlled by mixing two or more kinds of liquid crystal polymers each having a different wavelength region showing the circular dichroism. Accordingly, as shown in the example described below, an optical element showing a circular dichroism to a light of a visible light region can be easily obtained.

The formation of the optical element can be carried out by a method according to a conventional orientation treatment. For example, there is a method of forming an oriented film made up of polyimide, polyvinyl alcohol, etc., on a substrate, rubbing the film with a rayon cloth, etc., developing thereon the liquid crystal polymer, heating the liquid crystal polymer layer to a temperature of higher than the glass transition temperature and lower than the isotropic phase transition temperature, cooling the liquid crystal polymer layer lower than the glass transition temperature in the state that the liquid crystal polymer molecule is oriented to form a glass state, and forming a solid layer wherein the orientation is fixed. In this case, the optical element showing the circular dichroism can be formed by grandjean orienting the liquid crystal polymer molecule.

As the substrate described above, an appropriate material such as a film of a plastic, for example, triacetyl cellulose, polyvinyl alcohol, polyimide, polyarylate, polyester, polycarbonate, polysulfone, polyethersulfone, and an epoxy resin; or a glass plate, etc., can be used.

The solid layer of the liquid crystal polymer formed on the substrate can be used as it is as an optical element together with the substrate in a body or may be peeled from the substrate and can be used as an optical element comprising the film, etc.

The liquid crystal polymer can be developed on the substrate by a heat-melting system or as a solution thereof in a solvent. As the solvent, for example, methylene chloride, cyclohexanone, trichloroethylene, tetrachloroethane, N-methylpyrrolidone, and tetrahydrofuran can be properly used. The coat of the liquid crystal polymer can be carried out by a proper coating means such as bar coater, spinner, a roll coater, etc.

In regard to the thickness of the solid layer of the liquid crystal polymer formed, if the thickness is too thin, the liquid crystal polymer layer is hard to show the optical functions such as the circular dichroism, etc., and if the thickness is too thick, the liquid crystal polymer layer is poor in the uniform orientation property, whereby the optical functions such as the circular dichroism, etc., are not shown and further it takes a long time for the orientation treatment. Therefore, the thickness is preferably 0.1 to 30 $\mu$m, more preferably 0.3 to 20 $\mu$m, and particularly preferably 0.5 to 10 $\mu$m. In addition, in the case of forming the optical element, other polymer(s) than the liquid crystal polymer of the present invention and other various inorganic or organic additives such as a stabilizer, a plasticizer, metals, etc., can be, if necessary, compounded with the liquid crystal polymer of the present invention.

In the optical element of the present invention showing a circular dichroism, there is usually a limit in the wavelength region showing the circular dichroism in the case of the solid layer of the liquid crystal polymer of a single layer. The limit is usually a wide region of covering the wavelength region of about 100 nm but in the case of applying to the liquid crystal display device, etc., it is desired that the optical element shows a circular dichroism in the whole region of the visible light region or a wider region.

In the present invention, by laminating the solid layers of liquid crystal polymers each showing a circular dichroism to a light having a different wavelength, the wavelength region showing the circular dichroism can be enlarged. Such a lamination is useful, in addition to the enlargement of the wavelength region, in the point of coping with a wavelength shift of a slanting incident light. The lamination can be made by two or more layers in a combination of the layers each having a different central wavelength of the reflected circularly polarized light.

For example, an optical element showing the circular dichroism in a wide wavelength region of a visible light region can be formed by laminating 2 to 6 kinds of liquid crystal polymer solid layers each having the central wavelength of the reflected circularly polarized light of 300 to 900 nm, in the combination of reflecting the circularly polarized lights in the same direction using a combination of the layers each having a different central wavelength of the selective reflection, in particular, each at least 50 nm difference.

In laminating, it is preferable to attempt reducing surface reflection loss in each boundary using an adhesive or the like.

In addition, in the above-described combination, the point of combining the liquid crystal polymer layers each reflecting the circularly polarized light to a same direction aims at preventing each reflected circularly polarized light from becoming a different polarization state by making uniform the phase state of the circularly polarized light reflected at each layer and also improving the efficiency of re-utilizing the reflected circularly polarized lights in the case of re-utilizing the reflected circularly polarized lights via the reflection layers, etc.

The optical element of the present invention showing the circular dichroism separates an incident light into a right circularly polarized light and a left circularly polarized light based on the circular dichroism thereof and supplies as a transmitted light and a reflected light, and can improve the utilization efficiency of the light by re-utilizing the reflected light via the reflection layer, etc. Thus, the optical element of the present invention can be preferably used as an illuminator such as a polarizing plate, a back light, etc., in various apparatus such as a direct-vision type liquid crystal display device, etc.

The above-described illuminator can be obtained by a system of disposing the optical element showing the circular dichroism at the light coming out side in a side light type light guide of coming out an incident light from a side surface from one of the upper and the lower surfaces. Also, by disposing a reflection plate at the back surface of such a light conductive plate, the circularly polarized light reflected via the optical element is reflected via the reflection plate disposed at the back surface and can enter again to the optical element.

On the other hand, when the optical element is used as a polarizing film for obtaining a linearly polarized light, the optical element showing a circular dichroism is combined with a retardation layer of converting the circularly polarized light via the optical element showing the circular dichroism into a linearly polarized light. In this case, the retardation layer may be formed at the transmitting side or the reflecting side of the optical element showing the circular dichroism but in the case of the above-described illuminator, the retardation layer is formed at the transmitting side.

The retardation layer for converting the circularly polarized light to a linearly polarized light is for changing the phase of the circularly polarized light from the optical element and converting to a state having many linearly polarized light components. By converting to the state having many linearly polarized light components, a bright display by the direct incident to a liquid crystal cell and a bright display via the incident to a polarizing plate formed at a liquid crystal cell become possible.

Therefore, as the retardation layer, a retardation layer which can form many linearly polarized lights corresponding to the retardation of ¼ wavelength from the circularly polarized light via the optical element and can convert a light of other wavelength into a flat elliptically polarized light having the long diameter direction in parallel with the direction of the above-described linearly polarized light as parallel as possible and being near a linearly polarized light as near as possible, can be preferably used.

The retardation layer can be formed with a proper material and a transparent material which can give a uniform retardation is preferably used. In general, a retardation film made up of a stretched film of a plastic such as polycarbonate, the one-direction oriented film or the tortionally oriented film of a nematic liquid crystal polymer, etc., is used. The retardation of the retardation layer can be properly determined according to the wavelength region of the circularly polarized light by the optical element. For example, in a visible light region, from the point of the wavelength characteristics and the practicability, taking into consideration of that almost all retardation plates show the wavelength dispersion of a positive double refraction from the material characteristics, the retardation layer having a small retardation, in particular the retardation layer giving a retardation of 100 to 200 nm is preferably used in many cases.

The retardation layer can be formed as a single layer or two or more layers. In the case of the retardation layer comprising a single layer, the retardation layer showing the small wavelength dispersion of double refraction is preferred because in this case, the homogeneity of the polarized state of each wavelength can be obtained. On the other hand, the lamination of the retardation layers is effective for the improvement of the wavelength characteristics in a wavelength region and the combination thereof may be properly determined according to the wavelength region, etc.

In addition, in the case of laminating two or more retardation layers for a visible light region, it is preferred to include one or more retardation layers giving a retardation of 100 to 200 nm as described above as odd number layer(s) from the point of obtaining a light having many linearly polarized light components. As the layer(s) other than the layer of giving the retardation of 100 to 200 nm, it is preferred to use the layer(s) usually giving a retardation of 200 to 400 nm from the point of improving the wavelength characteristics but the layer(s) are not limited to these layer.

The present invention is described more practically below by the following examples but the present invention is not limited to them.

EXAMPLE 1

300 g of potassium hydroxide were dissolved in a mixed solution of 700 ml of ethanol and 100 ml of water. After dissolving 276 g of 4-hydroxybenzoic acid and a catalytic amount of potassium iodide in the solution, 177 g of ethylene chlorohydrin was gradually added to the mixture in a heated state followed by refluxing for about 15 hours. After distilling off ethanol from the reaction mixture obtained, the residue was added to 2 liters of water. After washing the aqueous solution obtained twice with diethyl ether, the solution was acidified by the addition of hydrochloric acid, and the precipitates thus formed were collected by filtration and dried, and recrystallized from ethanol to obtain 298 g (yield 82%) of 4-(2-hydroxyethoxy)benzoic acid.

Next, after dissolving 18.2 g of 4-(2-hydroxyethoxy) benzoic acid thus obtained in 300 ml of THF, 19.5 g of vinyl acrylate, 18 g of lipase PS, and a small amount of p-methoxyphenol were added to the solution followed by stirring for 3 hours at 40° C. After filtrating off lipase PS from the reaction mixture obtained, the filtrate was distilled under reduced pressure and solid residue formed was recrystallized from a 2/1 mixed solution of 2-butanone/hexane to obtain 17.5 g (yield 74%) of (4-(2-propenoyloxyethoxybenzoic acid.

On the other hand, after dissolving 10.0 g of isosorbide by stirring together with 0.5 g of p-toluenesulfonic acid•hydrate and 100 ml of THF at room temperature, 5.76 g of DHP diluted with 50 ml of THF was added dropwise to the solution over a period of 90 minutes, and then the mixture was stirred for 90 minutes at room temperature. Then, the solvent was distilled off from the reaction mixture obtained, the residue formed was dissolved in 250 ml of methylene chloride, and the solution was successively washed with 150 ml of a saturated aqueous sodium chloride solution, 150 ml of an aqueous solution of 1N-HCl, 150 ml of a saturated aqueous sodium chloride solution, 150 ml of a saturated aqueous sodium hydrogencarbonate solution, and 150 ml of a saturated aqueous sodium chloride solution. Thereafter, an organic layer formed was collected, dried with magnesium sulfate, and after distilling off the solvents, the residue formed was purified by silica gel column chromatography (methylene chloride/diethyl ether: 1/1) to obtain 4.79 g of isosorbide of which the hydroxyl group at one side was protected with THF.

Then, after stirring 4.21 g of THP one side-protected isosorbide described above, 2.96 g of 4-cyanobenzoic acid, 4.52 g of DCC, 0.28 g of DMA, and 110 ml of ethyl acetate for about 2 hours at room temperature, DCC urea deposited was filtrated off and then ethyl acetate was added to the filtrate such that the filtrate became 150 ml. Then, the filtrate was successively washed with 150 ml of a saturated aqueous sodium hydrogencarbonate solution, 150 ml of a saturated aqueous sodium chloride solution, 150 ml of an aqueous solution of 1N HCl, and 150 ml of a saturated aqueous sodium chloride solution, dried with magnesium sulfate, and the solvent was distilled off to obtain 7.81 g of the THP-protected ester. The purity of the product by liquid chromatography was 83%.

In a 300 ml egg-plant type flask, 7.44 g of the non-purified THP-protected ester obtained in the above step was dissolved in 75 ml of THF followed by refluxing and after adding 3 ml of an aqueous solution of 12N HCl to the solution followed by refluxing for 15 minutes, THF was distilled off from the solution. The residue formed was dissolved in 200 ml of methylene chloride, and the solution obtained was washed twice with 200 ml of a saturated aqueous sodium chloride solution and dried with magnesium sulfate. Then, after distilling off the solvent, the residue was purified by column chromatography (methylene chloride/diethyl ether: 6/1 to 0/1) to obtain 4.63 g of the above-described cyano-terminated isosorbide derivative (purity 97%, yield 91%).

Finally, after stirring 2.55 g of (4-(2-propenoyloxybenzoic acid) obtained above, 2.83 g of the cyano-terminated isosorbide derivative obtained above, 2.33 g of DCC, and 0.138 g of DMAP in 70 ml of methylene chloride for 4.5 hours at room temperature, deposited DCC urea was filtrated off and then methylene chloride was added to the filtrate such that the filtrate became 200 ml. Then, the filtrate was successively washed with 200 ml of an aqueous solution of 1N HCl, 200 ml of a saturated aqueous sodium chloride solution, 200 ml of saturated aqueous sodium hydrogencarbonate solution, and 200 ml of a saturated aqueous sodium chloride solution and then dried with magnesium sulfate. After distilling off the solvent from the filtrate, the residue formed was purified by column chromatography (methylene chloride/diethyl ether: 6/1) to obtain 1.39 g of the optically active monomer represented by the above-described formula (b1) (purity 90%, yield 23%).

Figure 1:
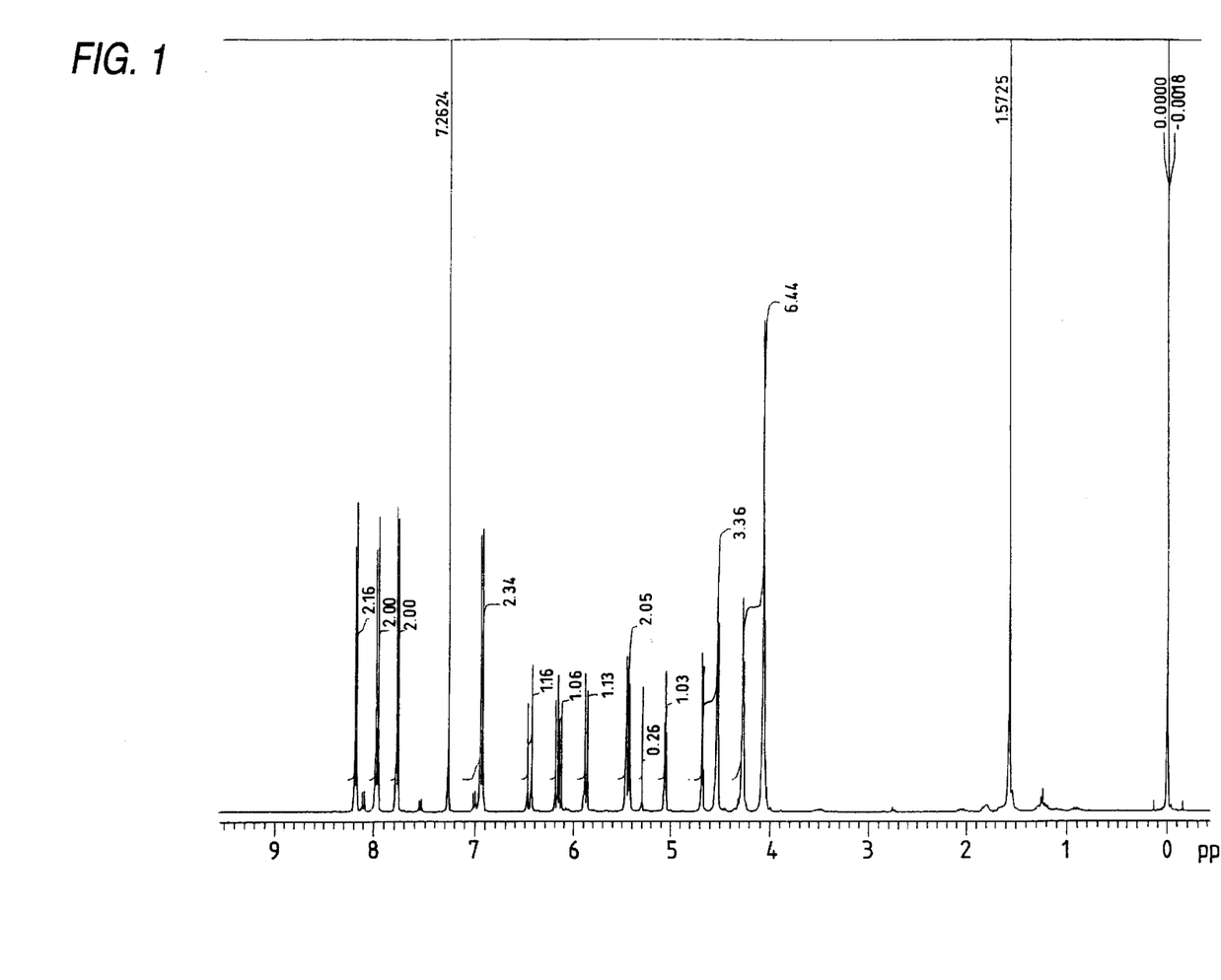
FIG. 1 is an analytical graph by proton NMR of the optically active monomer obtained in Example 1.
Figure 2:
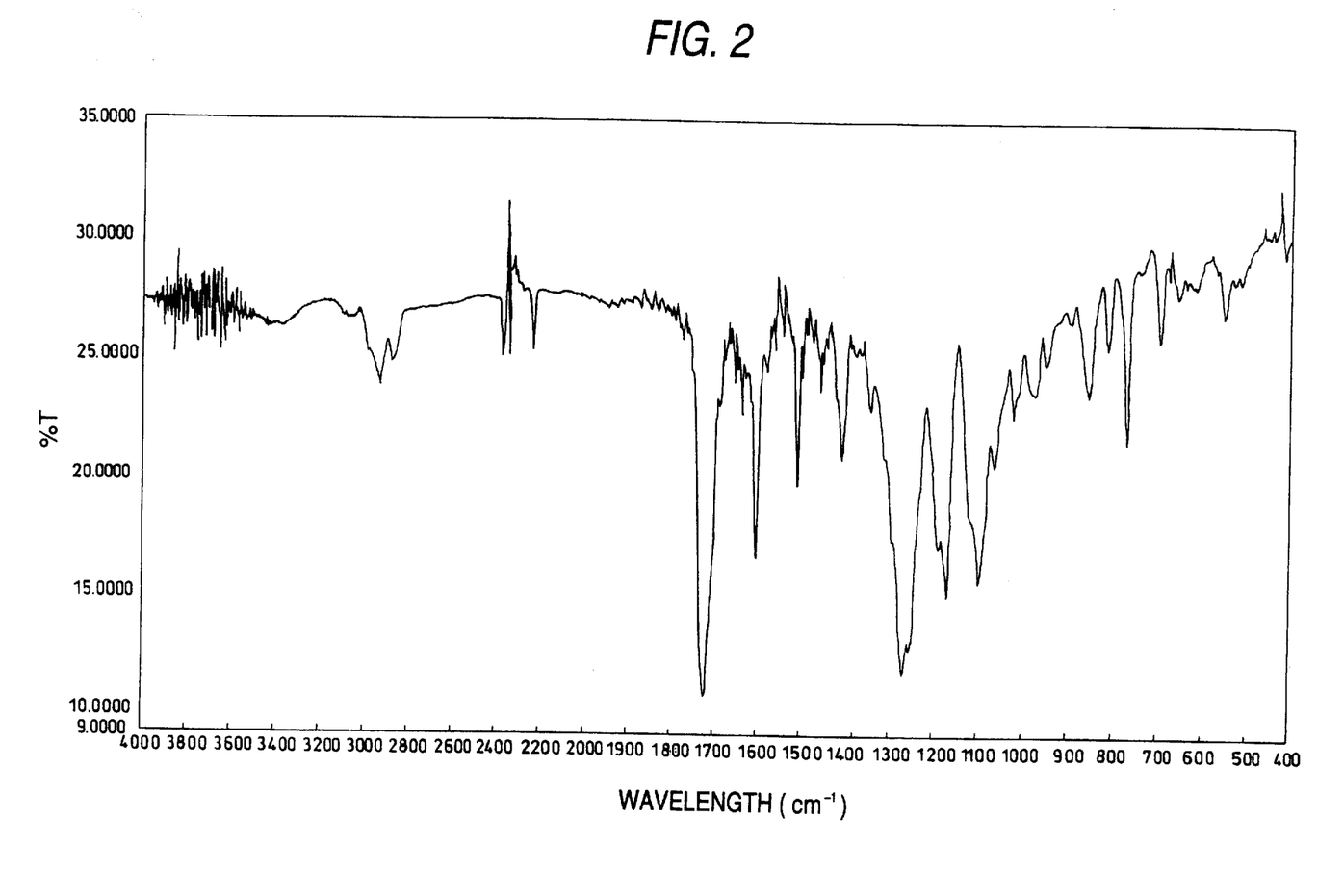
FIG. 2 is an analytical graph by IR of the optically active monomer obtained in Example 1.

The analytical results of the optically active monomer obtained by proton NMR and IR are shown in FIG. 1 and FIG. 2, respectively.

EXAMPLE 2

(d1)

In 16.5 ml of tetrahydrofuran were dissolved 0.168 g (0.31 mmol) of the optically active monomer represented by the formula (b1) and 1.56 g (3.78 mmols) of a monomer represented by the above-described formula (d1) by heating in a reaction vessel, after stabilizing the reaction system at a temperature of from 55 to 60° C., the inside atmosphere was replaced with a nitrogen gas, 0.5 ml of a tetrahydrofuran solution having dissolved therein 0.5 g of azobisisobutyronitrile was added dropwise to the solution in the absence of oxygen, and the polymerization was carried out for 3 hours. The reaction mixture obtained was gradually poured in 150 ml of diethyl ether with stirring to obtain precipitates of a white polymer and by collecting the precipitates by filtration and drying, a copolymer was obtained (yield 58%). The glass transition temperature of the copolymer was 90° C. and the copolymer showed a cholesteric structure having an isotropic phase transition temperature of 260° C.

EXAMPLE 3

According to Example 2, a copolymer having a glass transition temperature of 92° C. and showing a cholesteric structure having isotropic phase transition temperature of 275° C. was obtained using 0.15 g (0.28 mmol) of the optically active monomer represented by the formula (b1) and 1.64 g (3.98 mmols) of the monomer rrepresented by the above-described formula (d1).

EXAMPLE 4

According to Example 2, a copolymer having a glass transition temperature of 95° C. and showing a cholesteric structure having isotropic phase transition temperature of 282° C. was obtained using 0.13 g (0.24 mmol) of the optically active monomer shown by the formula (b1) and 1.96 g (4.76 mmols) of the monomer rrepresented by the above-described formula (d1).

EXAMPLE 5

Figure 3:
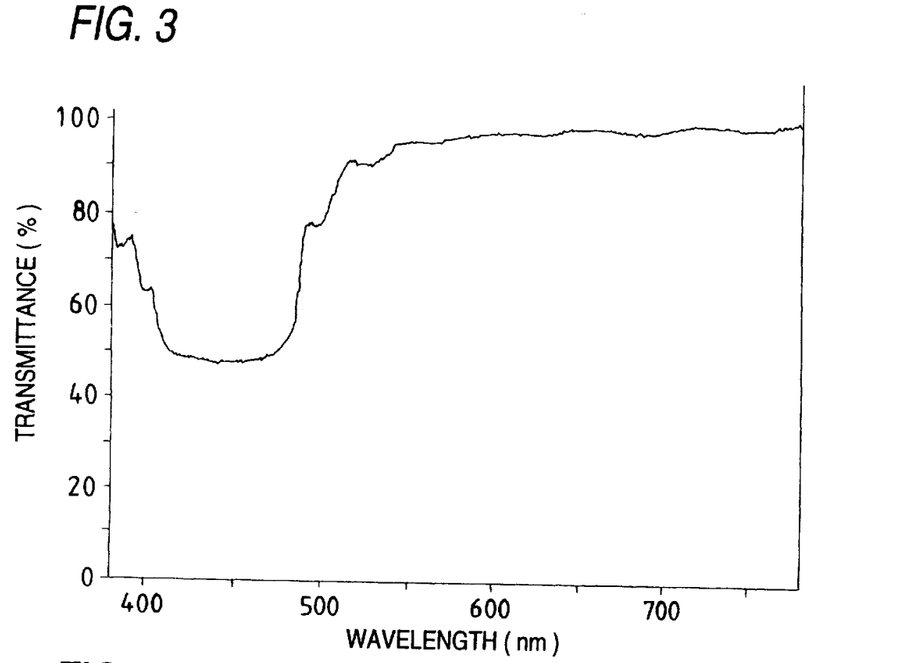
FIG. 3 is a graph showing the transmission characteristics of the optical element obtained in Example 5.

A polyvinyl alcohol layer of about 0.1 μm in thickness was formed on a glass plate, the layer was subjected to a rubbing treatment with a rayon cloth, a cyclohexanone solution of 30% by weight of the copolymer obtained in Example 2 was coated on the treated surface by a spinner and dried. Then, the coated layer was subjected to a heat-orientation treatment for 5 minutes at 150° C. and cooled to room temperature to fix the orientation of the liquid crystal polymer in a glass state. The thickness of the liquid crystal polymer was 2 μm and an optical element composed of the liquid crystal polymer and the glass plate in a body showed a circular dichroism reflecting a blue-purple light as a mirror plane and the wavelengths of the reflected light were from 405 to 485 nm. In addition, the transmitting characteristics of the optical element are shown in FIG. 3.

EXAMPLE 6

Figure 4:
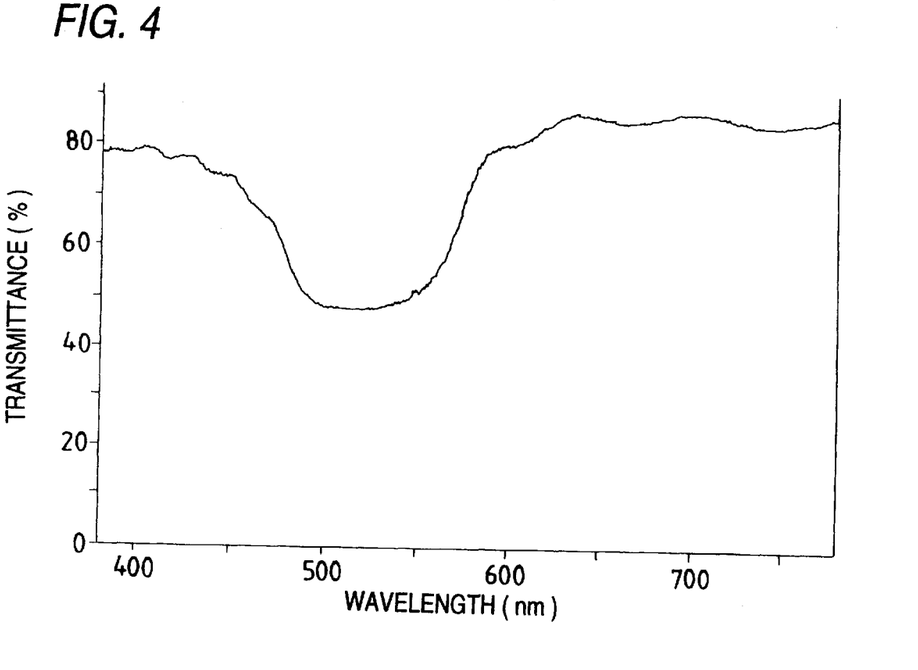
FIG. 4 is a graph showing the transmission characteristics of the optical element obtained in Example 6.

Example 5 was followed except for using the copolymer obtained in Example 3, to obtain an optical element showing a circular dichroism reflecting a red light as a mirror plane and wherein the wavelengths of the reflected light were from 480 to 555 nm. The transmitting characteristics of the optical element are shown in FIG. 4.

EXAMPLE 7

Figure 5:
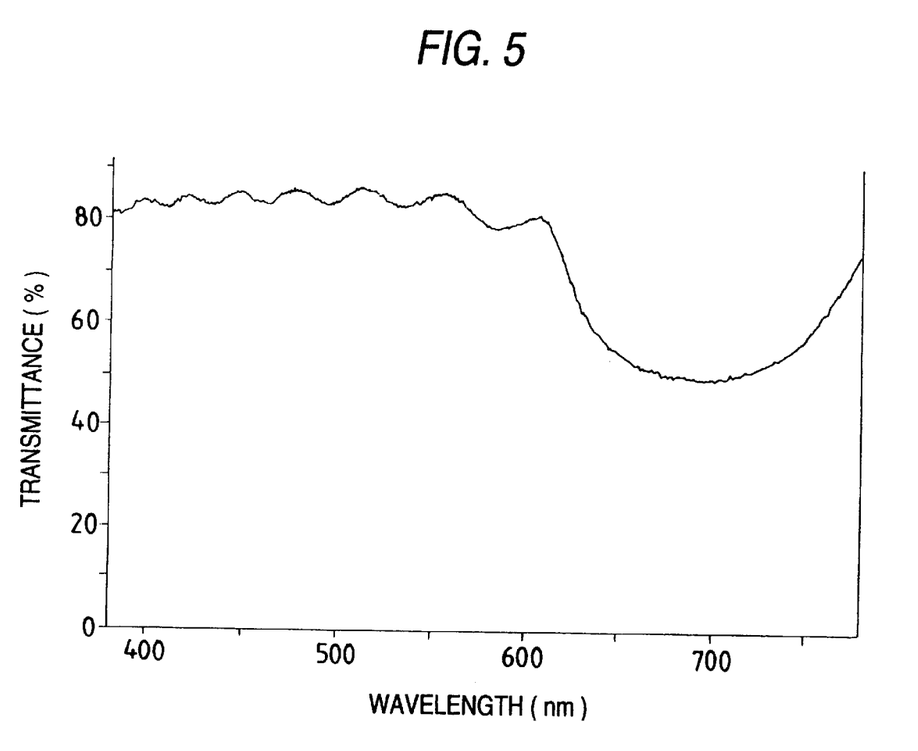
FIG. 5 is a graph showing the transmission characteristics of the optical element obtained in Example 7.

Example 5 was followed except for using the copolymer obtained in Example 4, to obtain an optical element showing a circular dichroism reflecting a red light as a mirror plane and wherein the wavelengths of the reflected light were from 642 to 740 nm. The transmitting characteristics of the optical element are shown in FIG. 5.

EXAMPLE 8

The optical elements obtained according to Examples 5, 6, and 7 were laminated via an acrylic pressure-sensitive adhesive layer respectively, to obtain an optical element showing a circular dichroism in wavelength regions of 405 to 555 nm and 642 to 740 nm based on the reflected light.

EXAMPLE 9

According to Example 5, an optical element was obtained using a mixture of 16.8 g of the homopolymer of the optically active monomer represented by the formula (b1) prepared according to Example 2 and 156 g of the homopolymer of the monomer represented by the above-described monomer (d1). The optical element showed a circular dichroism reflecting a blue-purple light as a mirror plane and the wavelength of the reflected light was from 415 to 495 nm.

In addition, in the above-described case, the homopolymer by the monomer of the formula (b1) had a glass transition temperature of 80° C. and an isotropic phase transition temperature of 210° C., and the orientation characteristics of the liquid crystal showed a cholesteric structure. Also, the homopolymer by the monomer of the formula (d1) had a glass transition temperature of 85° C. and an isotropic phase transition temperature of 287° C., and the orientation characteristics of the liquid crystal showed a nematic structure. Also, the above-described mixed polymer had a glass transition temperature of 90° C. and an isotropic transition temperature of 232° C., and the orientation characteristics of the liquid crystal showed a cholesteric structure.

EXAMPLE 10

50.0 g of isosorbide, 53.5 g of p-chlorobenzoic acid, and 1.4 g of DMAP were stirred together with 500 ml of methylene chloride on an ice bath, and 77.6 g of DCC dissolved in methylene chloride was added dropwise to the mixture. The mixture was stirred on an ice bath for 2.5 hours and at room temperature over night, deposited DCC urea was filtrated off, and methylene chloride was added to the filtrate such that the filtrate became 1000 ml. Then, the filtrate was successively washed with 1000 ml of an aqueous solution of 1N HCl, 1000 ml a saturated aqueous sodium chloride solution, 1000 ml of a saturated sodium hydrogen-carbonate solution, and 1000 ml of a saturated sodium chloride solution and dried with magnesium sulfate. Then, after distilling off the solvent from the filtrate, the residue was purified by silica gel column chromatography (methylene chloride/diethyl ether. 1/1) to obtain 14.2 g of a chlorophenyl-terminated isosorbide derivative.

Figure 6:
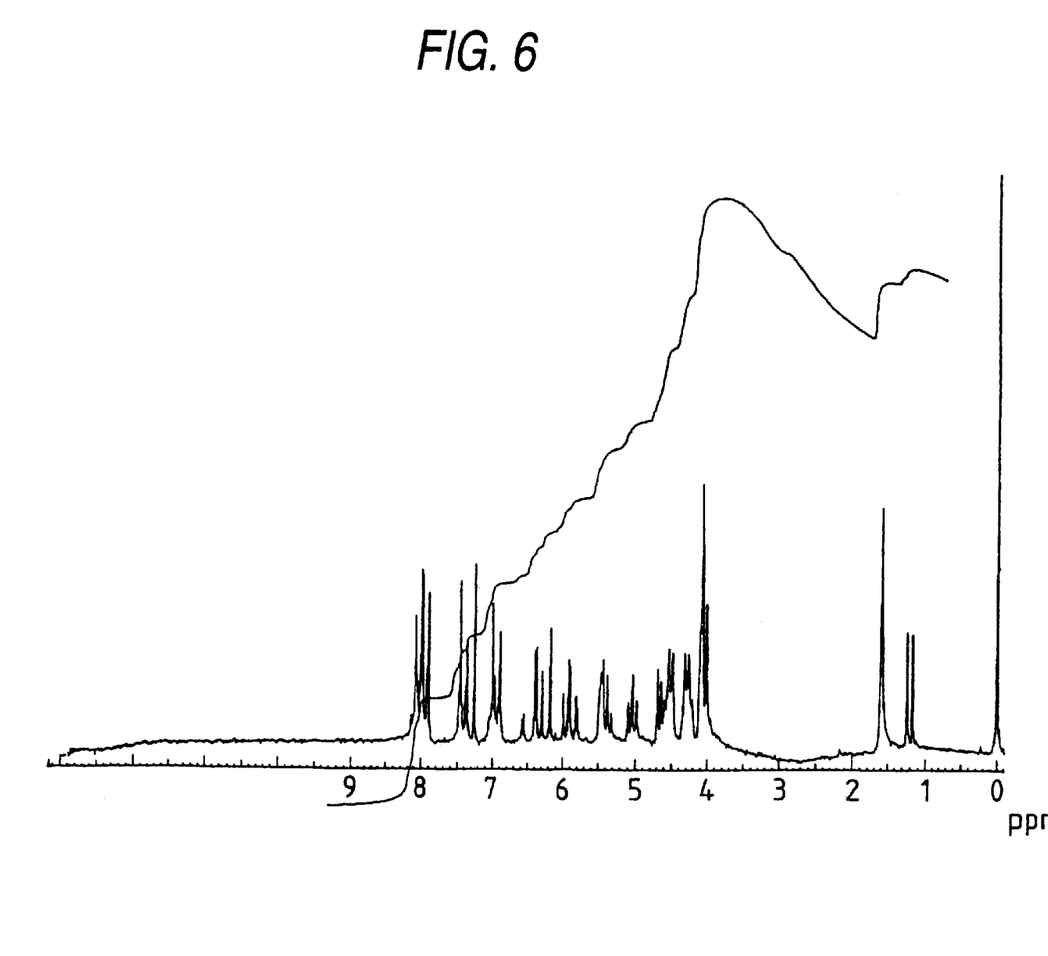
FIG. 6 is an analytical graph by proton NMR of the optically active monomer obtained in Example 10.
Figure 7:
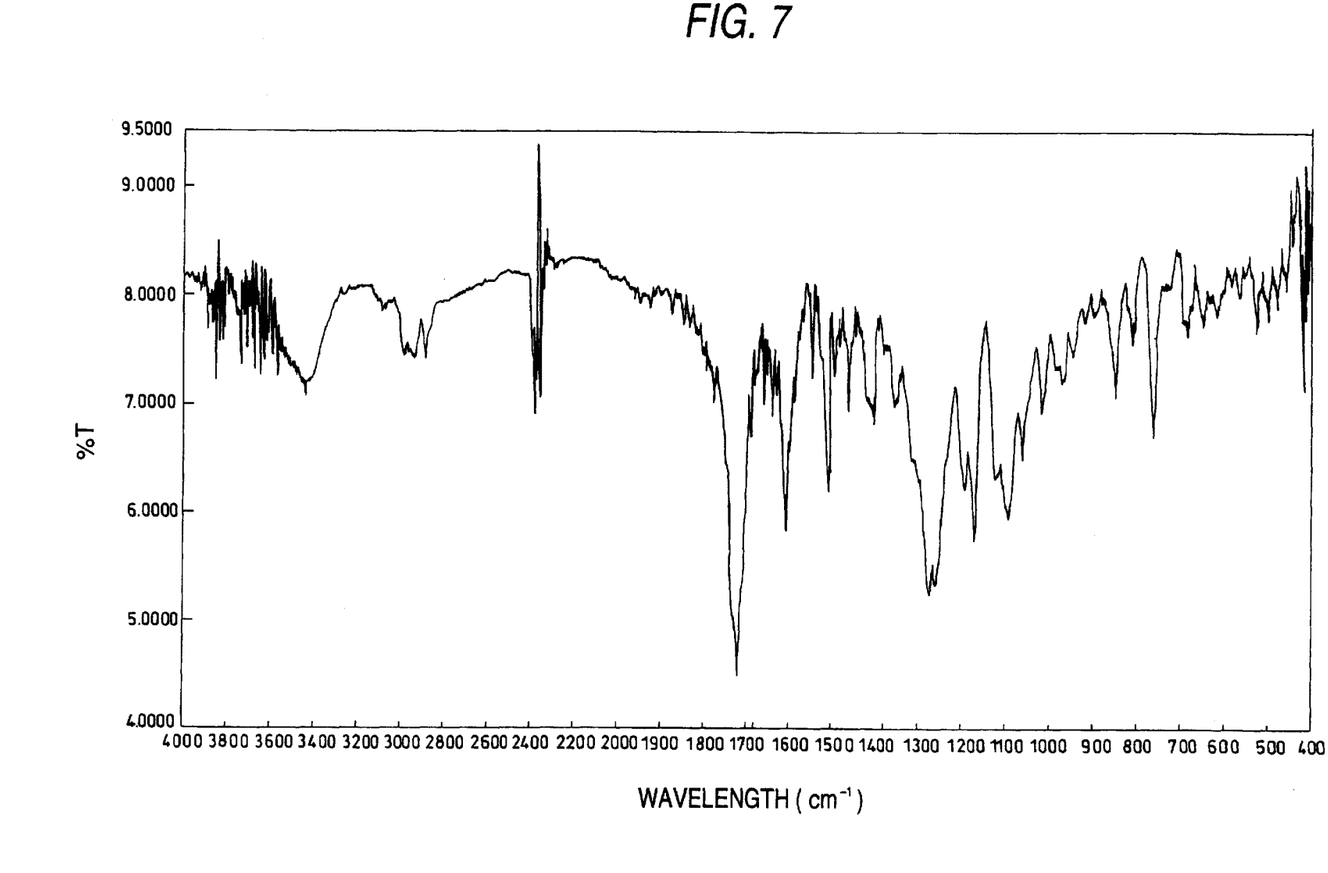
FIG. 7 is an analytical graph by IR of the optically active monomer obtained in Example 10.

Then, 14.2 g of the chlorophenyl-terminated isosorbide derivative described above and 12.9 g of 4-(2-propenoyloxyethoxy)benzoic acid were stirred together with 180 ml of methylene chloride on an ice bath, and after adding thereto 0.5 g of DMAP and a slight amount of dibutylhydroxytoluene, 11.3 g of DCC dissolved in 10 ml of methylene chloride was added little by little to the mixture. Then, the ice bath was removed and while the temperature of the reaction mixture was gradually raised to room temperature, the mixture was stirred overnight. DCC urea deposited was filtrated off and methylene chloride was added to the filtrate such that the filtrate became 500 ml. Then, the filtrate was successively washed with 500 ml of an aqueous solution of 1N HCl, 500 ml of a saturated aqueous sodium chloride solution, 500 ml of a saturated sodium hydrogen carbonate solution, and 500 ml of a saturated sodium chloride solution and dried with magnesium sulfate. After distilling off the solvent from the filtrate, the solid residue formed was recrystallized from a 70 ml/50 ml mixture of toluene/hexane to obtain 9.34 g of the optically active monomer represented by following formula (b2) (purity 95%). The analytical results of the optically active monomer by proton NMR and IR are shown in FIG. 6 and FIG. 7 respectively.

(b2)

EXAMPLE 11

In 95 g of a mixed solvent of 4 parts of dimethylacetamide/1 part of tetrahydrofuran were dissolved 1.50 g (2.98 mmols) of the optically active monomer represented by the above-described formula (b2) and 13.3 g (32.1 mmols) of the monomer represented by the above-described formula (d1) by heating in a reaction vessel, after stabilizing the mixture at a temperature of from 55 to 60° C., the inside atmosphere of the reaction vessel was replaced with a nitrogen gas, 2.0 ml of the above-described mixed solvent having dissolved therein 0.29 g of azobisisobutyronitrile was added dropwise to the mixture in the absence of oxygen, and the polymerization was carried out for 4.5 hours. After spontaneously filtering the reaction mixture, 120 ml of methanol was quickly added to the filtrate by stirring the filtrate vigorously to obtain precipitates of a white polymer. The precipitates were collected washed twice with 50 ml of a mixed solvent of 3 parts of methanol/2 parts of tetrahydrofuran and dried to obtain a copolymer. The copolymer had a glass transition temperature of 99° C. and an isotropic phase transition temperature of 262° C., and showed a cholesteric structure.

EXAMPLE 12

Figure 8:
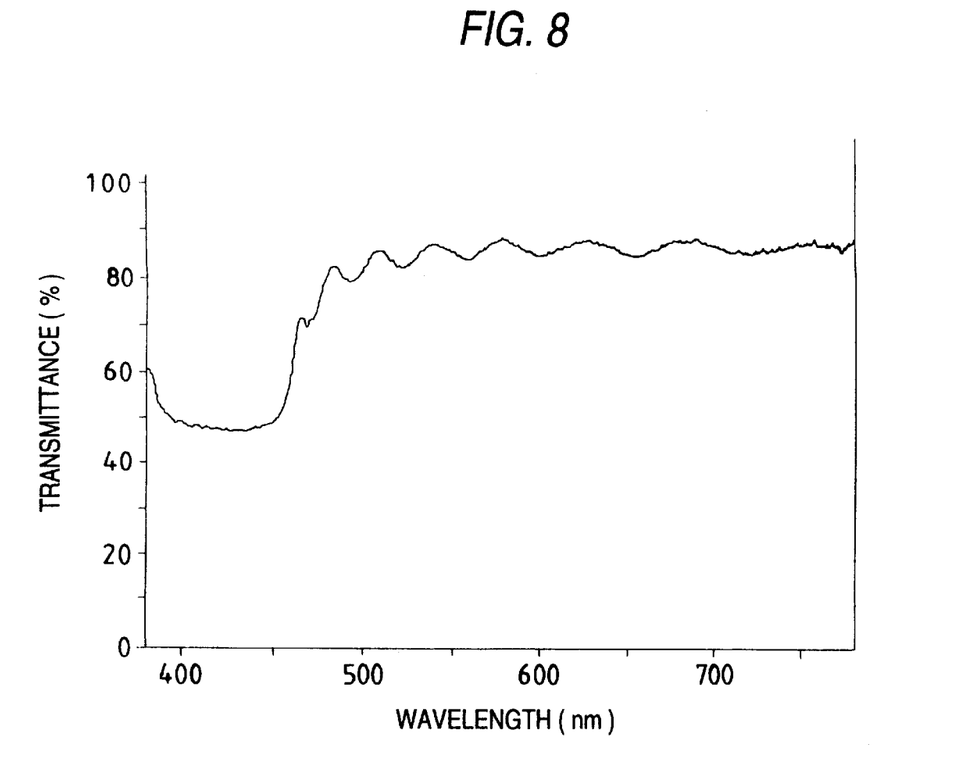
FIG. 8 is a graph showing the transmission characteristics of the optical element obtained in Example 12.

According to Example 5 except for using the copolymer obtained in Example 11, an optical element showing a circular dichroism reflecting a blue-purple light as a mirror plane, the wavelength of the reflected light being from 385 to 460 nm, was obtained. The transmitting characteristics of the optical element are shown in FIG. 8.

INDUSTRIAL APPLICABILITY

According to the optically active monomer of the present invention, a liquid crystal polymer excellent in the orientation property and the heat resistance can be obtained with a small amount thereof by a large torsion force thereof. Also, the liquid crystal polymer obtained can easily form a grandjean orientation film of a good monodomain state with a good film-forming property. As a result thereof, an optical element having circular dichroism, which is made up of the thin and light solid film of the liquid crystal, is hard to change the orientation state such as pitch, etc., at a practical temperature, and is excellent in the durability and the storage stability, can be formed with a good efficiency, and further an optical element, which can easily control a helical pitch of the cholesteric phase thereof and shows a circular dichroism in a visible light region, can be easily obtained.

What is claimed is:

1. An optical element showing a circular dichroism, comprising a solid layer of a grandjean oriented cholesteric liquid crystal phase comprising a side chain liquid crystal polymer having a structural unit comprising an optically active monomer for forming the side chain liquid crystal polymer represented by the following formula (a):

wherein $R^1$ represents a hydrogen atom or a methyl group, A represents an organic group, and B represents an organic group represented by the following formula (2a)

wherein Y represents OCO— or $0 \leq n \leq 3$; and $R^3$ represents —$C_dH_{2d+1}$ when n is 0 and represents —$OC_dH_{2d+1}$, —H, —CN, or —Cl when $1 \leq n \leq 3$, wherein d is $1 \leq d \leq 3$;

and the optical element has a retardation layer of converting a circularly polarized light to a linearly polarized light.

2. An optical element showing a circular dichroism, comprising a solid layer of a grandjean oriented cholesteric liquid crystal phase comprising a side chain liquid crystal polymer showing a cholesteric liquid crystal phase, comprising a copolymer comprising the optically active monomer for forming the side chain liquid crystal polymer represented by the following formula (a):

wherein $R^1$ represents a hydrogen atom or a methyl group, A is represented by the formula (a11): COO(CH$_2$)$_m$R$^2$Z wherein m is an integer of 1 to 6; $R^2$ is selected from the following groups:

and Z represents COO— or O—;

and B represents an organic group represented by the following formula (2a)

wherein Y represents OCO— or O—; $0 \leq n \leq 3$; and $R^3$ represents —$C_dH_{2d+1}$ when n is 0 and represents —$OC_dH_{2d+1}$, —H, —CN, or —Cl when $1 \leq n \leq 3$, wherein d is $1 \leq d \leq 3$;

and a monomer forming a polymer showing a nematic liquid crystal phase as components, said copolymer containing 1 to 40% by weight of the optically active monomer unit;

and the optical element has a retardation layer converting a circularly polarized light to a linearly polarized light.

3. An optical element showing a circular dichroism, comprising a solid layer of a grandjean oriented cholesteric liquid crystal phase comprising a side chain liquid crystal polymer showing a cholesteric liquid crystal phase, comprising a mixture of 1 to 40% by weight of a homopolymer comprising an optically active monomer for forming a side chain liquid crystal polymer represented by the following formula (a):

wherein $R^1$ represents a hydrogen atom or a methyl group, A is represented by the formula (a1): COO(CH$_2$)$_m$R$^2$Z wherein m is an integer of 1 to 6; $R^2$ is selected from the following groups:

and Z represents COO— or O—;

and B represents an organic group represented by the following formula (2a)

and wherein Y represents OCO— or O—; $0 \leq n \leq 3$; and $R^3$ represents —$C_dH_{2d+1}$ when n is 0 and represents —$OC_dH_{2d+1}$, —H, —CN, or —Cl when $1 \leq n \leq 3$, wherein d is $1 \leq d \leq 3$;

and 99 to 60% by weight of a homopolymer comprising a monomer forming a polymer showing a nematic liquid crystal phase;

and the optical element has a retardation layer of converting a circularly polarized light to a linearly polarized light.

4. An optical element as claimed in any one of claim 1, 2, or 3, wherein the optical element shows a circular dichroism in a visible light region.

5. An optical element as claimed in any one of claim 1, 2, or 3, wherein the optical element comprises a laminate of the solid layers of the side chain liquid crystal polymers each showing a circular dichroism in a light having a different wavelength.

6. A side chain liquid crystal polymer showing a cholesteric liquid crystal phase, comprising a copolymer comprising the optically active monomer for forming the side chain liquid crystal polymer represented by the following formula (a):

wherein $R^1$ represents a hydrogen atom or a methyl group, A is represented by the formula (a1): $COO(CH_2)_m R^2 Z$ wherein m is an integer of 1 to 6; $R^2$ is selected from the following groups:

and Z represents COO— or O—;

and B represents an organic group represented by the following formula (2a)

wherein Y represents OCO— or O—; $0 \leq n \leq 3$; and $R^3$ represents $-C_d H_{2d+1}$ when n is 0 and represents $-OC_d H_{2d+1}$, —H, —CN, or —Cl when $1 \leq n \leq 3$, wherein d is $1 \leq d \leq 3$;

and a monomer forming a polymer showing a nematic liquid crystal phase, said monomer having the formula wherein $R^4$ represents a hydrogen atom or a methyl group, e is an integer of 1 to 6; x represents $CO_2$— or OCO—; and p and q are 1 or 2 and satisfy p+q=3; and said copolymer containing 1 to 40% by weight of the optically active monomer unit.

7. A side chain liquid crystal polymer showing a cholesteric liquid crystal phase, comprising a mixture of 1 to 40% by weight of a homopolymer comprising an optically active monomer for forming a side chain liquid crystal polymer represented by the following formula (a):

wherein $R^1$ represents a hydrogen atom or a methyl group, A is represented by the formula (a1): $COO(CH_2)_m R^2 Z$ wherein m is an integer of 1 to 6; $R^2$ is selected from the following groups:

and Z represents COO— or O—;

and B represents an organic group represented by the following formula (2a)

and wherein Y represents OCO— or O—; $0 \leq n \leq 3$; and $R^3$ represents —$C_dH_{2d+1}$ when n is 0 and represents —$OC_dH_{2d+1}$, —H, —CN, or —Cl when $1 \leq n \leq 3$, wherein d is $1 \leq d \leq 3$;

and 99 to 60% by weight of a homopolymer comprising a monomer forming a polymer showing a nematic liquid crystal phase has the formula wherein $R^4$ represents a hydrogen atom or a methyl group, e is an integer of 1 to 6; x represents $CO_2$— or OCO—; and p and q are 1 or 2 and satisfy p+q=3.

* * * * *